(12) United States Patent
Mirkin et al.

(10) Patent No.: US 11,493,667 B2
(45) Date of Patent: Nov. 8, 2022

(54) PHOTONIC CRYSTALS COMPRISING NANOPARTICLES AND SPACER GROUPS

(71) Applicant: NORTHWESTERN UNIVERSITY, Evanston, IL (US)

(72) Inventors: Chad A. Mirkin, Wilmette, IL (US); Lin Sun, Evanston, IL (US); Haixin Lin, Evanston, IL (US); George C. Schatz, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 220 days.

(21) Appl. No.: 16/959,395

(22) PCT Filed: Jan. 31, 2019

(86) PCT No.: PCT/US2019/015965
§ 371 (c)(1),
(2) Date: Jun. 30, 2020

(87) PCT Pub. No.: WO2019/152594
PCT Pub. Date: Aug. 8, 2019

(65) Prior Publication Data
US 2021/0055455 A1 Feb. 25, 2021

Related U.S. Application Data

(60) Provisional application No. 62/624,328, filed on Jan. 31, 2018.

(51) Int. Cl.
| G02B 1/00 | (2006.01) |
| B22F 1/07 | (2022.01) |
| B22F 1/16 | (2022.01) |
| B22F 1/102 | (2022.01) |
| B22F 1/148 | (2022.01) |
| B82Y 20/00 | (2011.01) |
| B82Y 40/00 | (2011.01) |

(52) U.S. Cl.
CPC ........... *G02B 1/005* (2013.01); *B22F 1/07* (2022.01); *B22F 1/102* (2022.01); *B22F 1/148* (2022.01); *B22F 1/16* (2022.01); *B22F 2301/05* (2013.01); *B22F 2301/10* (2013.01); *B22F 2301/15* (2013.01); *B22F 2301/25* (2013.01); *B22F 2302/25* (2013.01); *B22F 2304/058* (2013.01); *B82Y 20/00* (2013.01); *B82Y 40/00* (2013.01)

(58) Field of Classification Search
CPC ........... G02B 1/005; B82Y 40/00; B22F 1/02
See application file for complete search history.

(56) References Cited

U.S. PATENT DOCUMENTS

| 6,859,304 B2 | 2/2005 | Miller et al. | |
| 2021/0055455 A1* | 2/2021 | Mirkin | G02B 1/005 |

OTHER PUBLICATIONS

Waterhouse et al., Opal and inverse opal photonic crystals: Fabrication and characterization, Polyhedron, 26(2):356-368 (2007).

(Continued)

*Primary Examiner* — Mark V Prenty
(74) *Attorney, Agent, or Firm* — Marshall, Gerstein & Borun LLP (57) ABSTRACT

Provided herein are methods of preparing three-dimensional photonic crystals having tunable optical properties and control over stopband location and width, the three-dimensional photonic crystals comprising nanoparticles and spacer groups.

20 Claims, 7 Drawing Sheets
Specification includes a Sequence Listing.

(56) References Cited

OTHER PUBLICATIONS

Xiao et al., Loss-free and active optical negative-index metamaterials, Nature, 466:735-738 (2010).
Yablonovitch et al., Photonic band structure: The face-centered-cubic case employing nonspherical atoms, Phys. Rev. Lett., 67:2295-2298 (1991).
Akselrod et al., Probing the mechanisms of large purcell enhancement in plasmonic nanoantennas, Nat. Photonics, 8:835-840 (2014).
Armstrong et al., Artificial opal photonic crystals and inverse opal structures-Fundamentals and applications from optics to energy storage, J. Mater. Chem. C. Mater. Opt. Electron Devices, 3:6109-6143 (2015).
Arsenault et al., From colour fingerprinting to the control of photoluminescence in elastic photonic crystals, Nat. Mater., 5:179-184 (2006).
Boles et al., Self-assembly of colloidal nanocrystals: From intricate structures to functional materials, Chem. Rev., 116(18):11220-11289 (2016).
Engheta, Circuits with light at nanoscales: Optical nanocircuits inspired by metamaterials, Science, 317:1698-1702 (2007).
Esteban et al., Strong coupling of single emitters interacting with phononic infrared antennae, New J. Phys., 16:013052 (2014).
Freymann et al., Bottom-up assembly of photonic crystals, Chem. Soc. Rev., 42:2528-2554 (2013).
García-Santamaría et al., Synthetic opals based on silica-coated gold nanoparticles, Langmuir, 18(11):4519-4522 (2002).
Giljohann et al., Gold nanoparticles for biology and medicine, Angew. Chem. Int. Ed. Engl., 49(19):3280-3294 (2010).
Hagemann et al., Optical constants from the far infrared to the x-ray region: Mg, Al, Cu, Ag, Au, Bi, C, and Al2O3, J. Opt. Soc. Am., 65(6):742-744 (1975).
Halas et al., Plasmons in strongly coupled metallic nanostructures, Chem. Rev., 111:3913-3961 (2011).
Henzie et al., Self-assembly of uniform polyhedral silver nanocrystals into densest packings and exotic superlattices, Nat. Mater., 11:131-137 (2011).
Hermatschweiler et al., Fabrication of silicon inverse woodpile photonic crystals, Adv. Funct. Mater., 17(14):2273-2277 (2007).
Huang et al., A surface-emitting laser incorporating a high-index-contrast subwavelength grating, Nat. Photonics., 1:119-122 (2007).
International Application No. PCT/US2019/015965, International Preliminary Reporton Patentability, dated Aug. 13, 2020.
International Application No. PCT/US2019/015965, International Search Report and Written Opinion, dated Apr. 26, 2019.
Jang et al., Highly tolerant a-Si distributed Bragg reflector fabricated by oblique angle deposition, Opt. Mater. Express, 1(3):451-457 (2011).
Johnson et al., Optical Constants of the Noble Metals, Phys. Rev., 6(12):4370-4379 (1972).
Jones et al., Programmable materials and the nature of the DNA bond, Science, 347:1260901 (2015).
Kabashin et al., Plasmonic nanorod metamaterials for biosensing, Nat. Mater., 8:867-871 (2009).
Karg et al., Self-assembly of tunable nanocrystal superlattices using poly-(nipam) spacers, Adv. Funct. Mater., 21:4668-4676 (2011).
Kelly et al., The optical properties of metal nanoparticles: The influence of size, shape, and dielectric environment, J. Phys. Chem. B., 107(3):668-677 (2003).
Kim et al., Transmutable nanoparticles with reconfigurable surface ligands, Science, 351:579-582 (2016).
Kubo et al., Tunability of the refractive index of gold nanoparticle dispersions, Nano Lett., 7:3418-3423 (2007).
Laor et al., The role of surface roughness in surface enhanced Raman spectroscopy (SERS): The importance of multiple plasmon resonances, Chem. Phys. Lett., 82:566-570 (1981).
Liu et al., Strain management of AlGaN-based distributed Bragg reflectors with GaN interlayer grown by metalorganic chemical vapor deposition, Appl. Phys. Lett., 109:081103 (2016).
Luo et al., Negative refraction without negative index in metallic photonic crystals, Opt. Express, 11:746-754 (2003).
Macfarlane et al., Nanoparticle superlattice engineering with DNA, Science, 334:204-208 (2011).
Maldovan et al., Diamond-structured photonic crystals, Nat. Mater., 3:593-600 (2004).
Marzán et al., Tailoring surface plasmons through the morphology and assembly of metal nanoparticles, Langmuir, 22:32-41 (2006).
Mason et al., Contraction and expansion of stimuli-responsive DNA bonds in flexible colloidal crystals, J. Am. Chem. Soc., 138:8722-8725 (2016).
Mirkin et al., A DNA-based method for rationally assembling nanoparticles into macroscopic materials, Nature, 382:607-609 (1996).
Miyake et al., Fabrication of three-dimensional photonic crystals using multibeam interference lithography and electrodeposition, Adv. Mater., 21(29):3012-3015 (2009).
Nelson et al., Epitaxial growth of three-dimensionally architectured optoelectronic devices, Nat. Mater., 10:676-681 (2011).
Norris, Photonic crystals, A view of the future, Nat. Mater., 6:177-178 (2007).
O'Brien et al., Universal Noble Metal Nanoparticle Seeds Realized Through Iterative Reductive Growth and Oxidative Dissolution Reactions, J. Am. Chem. Soc., 136(21):7603-7606 (2014).
O'Brien et al., Programming colloidal crystal habit with anisotropic nanoparticle building blocks and DNA bonds, J. Am. Chem. Soc., 138:14562-14565 (2016).
Oh et al., Fabrication of wafer-scale polystyrene photonic crystal multilayers via the layer-by-layer scooping transfer technique, J. Mater. Chem., 21:14167-14172 (2011).
Park et al., Directional emission from dye-functionalized plasmonic DNA superlattice microcavities, Proc. Natl. Acad. Sci. U.S.A., 114:457-461 (2017).
Ross et al., Optical properties of one-, two-, and threedimensional arrays of plasmonic nanostructures, J. Phys. Chem. C., 120:816-830 (2016).
Shevchenko et al., Structural diversity in binary nanoparticle superlattices, Nature, 439:55-59 (2006).
Shiles et al., Self-consistency and sum-rule tests in the Kramers-Kronig analysis of optical data: Applications to aluminum, Phys. Rev. B, 22(4):1612-1628 (1980).
Sigalas et al., Metallic photonic band-gap materials, Phys. Rev. B., 52:11744-11751 (1995).
Smith et al., Electromagnetic parameter retrieval from inhomogeneous metamaterials, Phys. Rev. E. Stat. Nonlin. Soft. Matter. Phys., 71:036617 (2005).
Sun et al., Design principles for photonic crystals based on plasmonic nanoparticle superlattices, PNAS., 115(28):7242-7247 (2018).
Sun et al., Polarization-Dependent Optical Response in Anisotropic Nanoparticle-DNA Superlattices, Nano Lett. 17(4):2313-2318 (2017).
Tao et al., Self-organized silver nanoparticles for three-dimensional plasmonic crystals, Nano Lett., 8:4033-4038 (2008).
Taubert et al., Octave-wide photonic band gap in three-dimensional plasmonic Bragg structures and limitations of radiative coupling, 3:291 (2012).
Tsai et al., Three-dimensional photonic band gaps in woven structures, J. Phys. Condens Matter, 10:753 (1998).
Vlasov et al., On-chip natural assembly of silicon photonic bandgap crystals, Nature, 414:289-293 (2001).

* cited by examiner

FIG. 3A $$\text{volume fraction} = \frac{NP \; V_{sphere}}{A * (2r)}$$

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetic polynucleotide -continued

```
<400> SEQUENCE: 1
tcaactattc ctacctacaa aaaaaaaash                                    30

<210> SEQ ID NO 2
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 2
gtaggtagga atagttgaat tttttttttt tactgagcag cactgatttt ttttttttta   60
gcgc                                                                64

<210> SEQ ID NO 3
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 3
aaaaaaaaaa aaatcagtgc tgctcagtaa aaaaaaaaaa                         40

<210> SEQ ID NO 4
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 4
aaaaaaaaaa                                                          10
```

PHOTONIC CRYSTALS COMPRISING NANOPARTICLES AND SPACER GROUPS

This application is a U.S. National Application of International Patent Application No. PCT/US19/15965, filed Jan. 31, 2019, which claims the benefit of U.S. Provisional Patent Application No. 62/624,328, filed Jan. 31, 2018, both of which are herein incorporated by reference in their entirety.

STATEMENT OF GOVERNMENT SUPPORT

This invention was made with government support under grant number DE-SC0000989 awarded by the U.S. Department of Energy, grant number FA9550-12-1-0280 awarded by the U.S. Air Force Office of Scientific Research, and grant number 12204315 awarded by the U.S. Air Force Office of Scientific Research. The government has certain rights in this invention.

FIELD OF THE DISCLOSURE

The disclosure relates generally to methods of preparing three-dimensional photonic crystals. More particularly, the disclosure relates to methods of preparing three-dimensional photonic crystals having tunable optical properties and control over stopband location and width, the three-dimensional photonic crystals comprising nanoparticles and spacer groups.

BACKGROUND

Photonic crystals (PCs) are materials with periodically varied refractive indices, in which optical control is achieved by refractive index contrast and diffraction. When the effective wavelength of light satisfies the Bragg criterion, namely when the wavelength is on the order of twice the periodicity, light propagation in certain directions inside the material is "forbidden." This gives rise to a photonic band gap (PBG). Due to this property, PCs have been intensively studied for potential use in a wide range of technologies, such as semiconductor lasers, optical integrated circuits, optical switches, and solar cells. In addition, they are commercially used for light emitting diodes, sensors, and optical fibers.

Conventionally, PCs are structures made of dielectric materials (e.g., polymers and semiconductors) and prepared via top-down or bottom-up fabrication processes. Top-down processes typically involve drilling holes in dielectric materials along certain crystal orientations with either conventional mechanical tools or electron-beam lithography. "Woodpile" photonic structures also have been generated by cross-stacking dielectric materials. More recently, the colloidal assembly of monodisperse spheres of silica, polystyrene, and other polymer materials has become a heavily used method to generate PCs; such bottom-up assembly techniques are attractive because they are often simpler, less expensive, and more scalable than top down approaches. The resulting PCs, also known as opals, are close-packed. In addition, the spherical particle lattice that defines a PC has been used as a template to create inverse opals, where a high refractive index material is backfilled into the gaps between the spheres, and the spheres are subsequently removed to create spheres of air.

Considerable effort has been spent on incorporating dielectric materials with high refractive indices into PCs. However, there remain several challenges, including overcoming the large strain that results from interfacing materials with large lattice mismatches, poor crystal quality, and low index contrast. Moreover, since the high-index materials are closely spaced and sometimes touching, any plane along the light propagation direction is always composed of a mixture of both high- and low-index layers, which greatly reduces the index contrast.

SUMMARY

The disclosure provides a method of forming a three-dimensional photonic crystal having a band gap having a center wavelength, $\lambda_0$, in a range of about 300 nm to about 10 μm, comprising (a) selecting a nanoparticle, wherein the nanoparticle comprises a plasmonic nanoparticle or a high index dielectric nanoparticle having a refractive index, $n_h$, in a range of about 2 to about 30; (b) selecting a spacer group having a refractive index, $n_l$, in a range of about 1 to about 3, and a length, d, wherein $n_h$ is greater than $n_l$; and (c) admixing a plurality of the nanoparticles and a plurality of spacer groups to form a three-dimensional photonic crystal comprising alternating nanoparticles and spacer groups; wherein (i) the spacer group length, d, is selected such that the maximum reflectance in the reflectance spectrum, $R_{max}$, is greater than or equal to 0.80 when the photonic crystal is irradiated with an incident light having a wavelength $\lambda_0$; and (ii) the photonic crystal comprises a number of nanoparticle layers, N, normal to the incident light, such that $R_{max}$ is greater than or equal to 0.8 when the photonic crystal is irradiated with the incident light having a wavelength $\lambda_0$, thereby forming a three-dimensional photonic crystal having a band gap having a center wavelength, $\lambda_0$, in a range of about 300 nm to about 10 μm.

For the photonic crystals and methods disclosed herein, optional features, including but not limited to components, conditions, and steps are contemplated to be selected from the various aspects, embodiments, and examples provided herein.

Further aspects and advantages will be apparent to those of ordinary skill in the art from a review of the following detailed description. While the photonic crystals and their methods of making are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For a more complete understanding of the disclosure, reference should be made to the following detailed description and accompanying drawings wherein:

FIG. 7 further shows the crystal symmetry of 13 Bravais lattices.

DETAILED DESCRIPTION

Provided herein are methods of preparing three-dimensional photonic crystals comprising plasmonic or high-index dielectric nanoparticles and spacer groups. Three-dimensional photonic crystals can advantageously demonstrate photonic properties when irradiated with light in any one of the dimensions of the crystal. In contrast, one dimensional photonic crystals and two-dimensional photonic crystals demonstrate photonic properties only when irradiated with light in one or two specific dimensions, respectively. The method provided herein provides a three-dimensional photonic crystal having a band gap having a center wavelength, $\lambda_0$, in a range of about 300 nm to about 10 μm, the method comprising the steps of (a) selecting a nanoparticle, wherein the nanoparticle comprises a plasmonic nanoparticle or a high index dielectric nanoparticle having a refractive index, $n_h$, in a range of about 2 to about 30; (b) selecting a spacer group having a refractive index, $n_l$, in a range of about 1 to about 3, and a length, d, wherein $n_h$ is greater than $n_l$; and (c) admixing a plurality of the nanoparticles and a plurality of spacer groups to form a three-dimensional photonic crystal comprising alternating nanoparticles and spacer groups; wherein (i) the spacer group length, d, is selected such that the maximum reflectance in the reflectance spectrum, $R_{max}$, is greater than or equal to 0.80 when the photonic crystal is irradiated with an incident light having a wavelength $\lambda_0$; and (ii) the photonic crystal comprises a number of nanoparticle layers, N, normal to the incident light, such that $R_{max}$ is greater than or equal to 0.8 when the photonic crystal is irradiated with the incident light having a wavelength $\lambda_0$.

Conceptualized in the one-dimensional case, the photonic crystal (PC) can be viewed as periodically alternating layers of high- and low-index materials or a distributed Bragg reflector, and the photonic band gap (PBG) can be identified as the spectral region with high reflectance (low transmittance) in the far-field spectra, in other words a stopband in the reflectance spectra. As used herein, "photonic band gap," "band gap," and "stopband" are used interchangeably. For incident angles perpendicular to the layers, the Bragg condition is best met when the optical length of each layer of the PC is a quarter of the relevant wavelength, equation (1).

$$\frac{\lambda_0}{4} = d_h n_h = d_l n_l \tag{1}$$

Here, $\lambda_0$ is the center wavelength of the photonic band, and $d_h$, $n_h$ and $d_l$, $n_l$ are the thicknesses and refractive indices of the high- and low-index materials, respectively. The higher the contrast between the high and low refractive indices, the broader the photonic bandwidth, as governed by equation (2):

$$\frac{\Delta\lambda_0}{\lambda_0} = \frac{4}{\pi} \text{ARCSIN}\left(\frac{n_h - n_l}{n_h + n_l}\right) \tag{2}$$

where $\Delta\lambda_0$ and $\lambda_0$ are the width and center wavelength of the band. The maximum reflectance ($R_{max}$) is not only dependent on the index contrast but also on the number of layers through the equation:

$$R_{max} = \left[\frac{n_0(n_h)^{2N} - n_s(n_l)^{2N}}{n_0(n_h)^{2N} + n_s(n_l)^{2N}}\right]^2 \tag{3}$$

wherein $n_0$ and $n_s$ are the indices of the top and bottom layers outside of the crystal, and N is the number of layers of the high-index material.

For all of the fabrication methods for photonic crystals, one important parameter for achieving large PBG and high reflectance is the refractive index contrast between the high- and low-index materials, the importance of which can be seen in equations (1)-(3) above. Moreover, as can be seen in equation (1), in order to satisfy the Bragg condition at certain wavelengths, the thickness of each layer can be reduced by using materials with a higher index, which is important for the miniaturization of devices.

Plasmonic or High-Index Dielectric Nanoparticles

In general, the nanoparticles used in the methods of the disclosure can be any plasmonic or high-index dielectric nanoparticles. Methods of forming nanoparticles are well known in the art. A nanoparticle is a "high-index" nanoparticle if the index of refraction of the nanoparticle is greater than the index of refraction of the spacer group. In embodiments, the index of refraction of the nanoparticle can be at least 2 and/or up to about 30, for example, about 2, 3, 4, 5, 6, 7, 8, 9, 10, 11, 12, 13, 14, 15, 16, 17, 18, 19, 20, 21, 22, 23, 24, 25, 26, 27, 28, 29, or 30. In embodiments, the difference between the index of refraction of the high-index nanoparticle and the index of refraction of the spacer group, Δn, can be 0.1 index of refraction units, for example, at least 0.1, at least 0.3, at least 0.5, at least 0.7, at least 0.9, at least 1.0, at least 1.5, at least 2, at least 2.5, at least 3, or at least 5 index of refraction units and up to 27, up to 25, up to 20, up to 18, up to 15, up to 13, up to 10, up to 8, up to 6, up to 4, or up to 2 index of refraction units. In general, the higher the contrast between the refractive indices of the plasmonic or high-index material and spacer group, the broader the width of the photonic band gap of the resulting three-dimensional photonic crystal.

Figure 9:
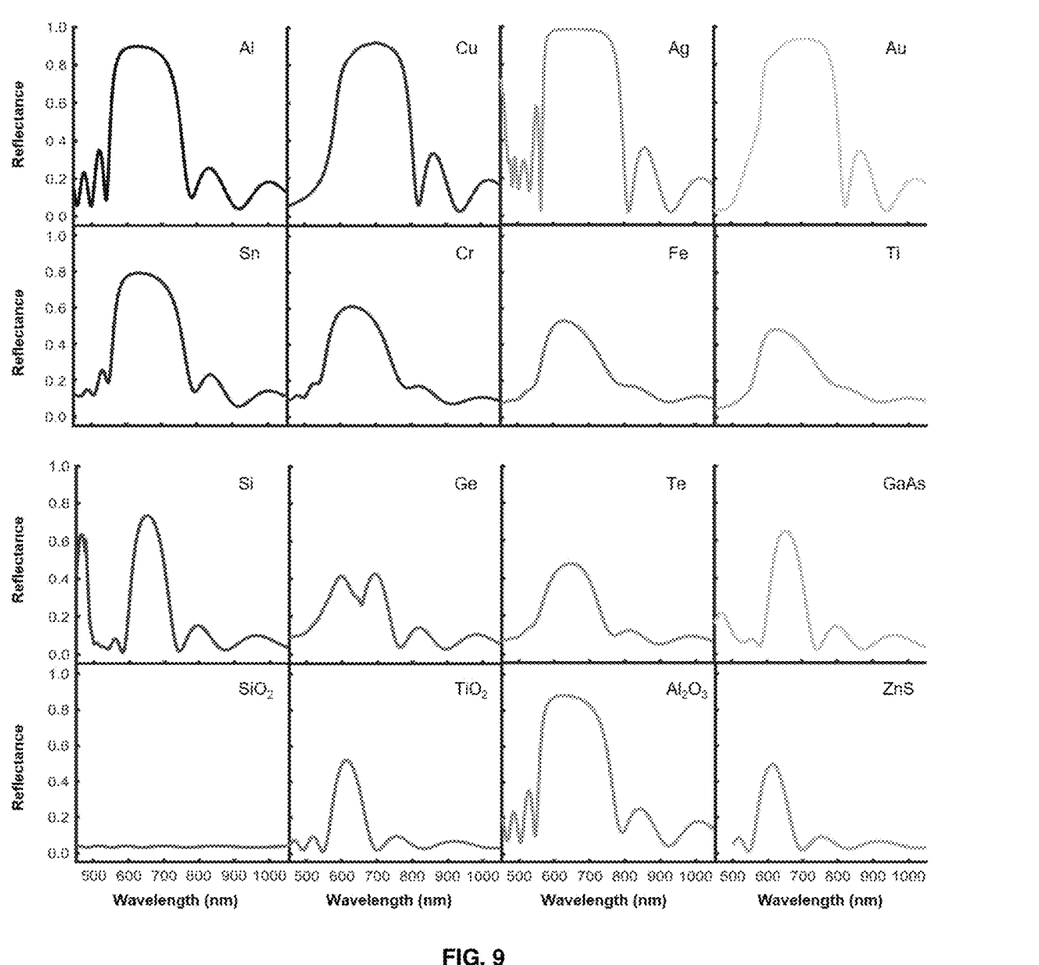
FIG. 9 shows reflectance spectra of lattices made with different materials, wherein (top) the nanoparticle comprises plasmonic materials, (second row) metallic and poorly plasmonic materials, and (bottom two rows) dielectric materials.

The plasmonic or high-index dielectric nanoparticle can comprise a plasmonic metal nanoparticle. The free electrons in plasmonic metal nanoparticles are confined and interact strongly with light, giving rise to a localized surface plasmon resonance (LSPR). The frequency of the LSPR is dependent upon the nanoparticle's size, shape, and the dielectric environment. $R_{max}$ is limited by absorption (i.e., what is absorbed cannot be reflected). Plasmonic metal nanoparticles are absorptive close to the plasmon resonance frequency, and absorption is relatively small at frequencies well away from the plasmon frequency. The plasmonic metal nanoparticles can comprise a plasmonic metal selected from the group consisting of gold, silver, copper, platinum, palladium, nickel, aluminum, gallium, indium, lithium, sodium, potassium, rubidium, magnesium, calcium, strontium, and a combination thereof. In some embodiments, the plasmonic metal nanoparticles comprise a plasmonic metal selected from the group consisting of gold, silver, and a combination thereof. In embodiments, the plasmonic metal nanoparticles comprise gold. In embodiments, the plasmonic metal nanoparticles comprise silver. In contrast to photonic crystals comprising plasmonic metals, it was found that superlattices comprising metallic nanoparticles having poor plasmonic properties (e.g., titanium, chromium, and iron), but having the same lattice parameters as the photonic crystal, demonstrate much weaker stopband properties. This is demonstrated in FIG. 9, which shows reflectance spectra of lattices made with different materials as calculated by FDTD simulation. In particular, the reflectance spectra for plasmonic nanoparticles show advantageously broad stopbands (i.e., the range of wavelengths for which the maximum reflectance ($R_{max}$) is greater than or equal to 0.8) while the reflectance spectra for the metallic and poorly plasmonic nanoparticles have low reflectance (e.g., less than 0.8) with a narrow $R_{max}$ range. The nanoparticles were spherical with a 54 nm radius and the nanoparticle layer volume fraction was 0.153. The spacer layer had a refractive index of 1.46, the lattice parameters were fixed as cubic lattices with a 200 nm lattice constant, and 7 layers were simulated.

In some embodiments, the nanoparticles can comprise doped metal oxides and/or transparent conducting oxides. In embodiments, the nanoparticles comprise gallium doped zinc oxide, aluminum doped zinc oxide, cesium doped indium oxide, tin doped indium oxide, or a combination thereof. In embodiments, the nanoparticles comprise gallium doped zinc oxide, aluminum doped zinc oxide, or a combination thereof. In embodiments, the nanoparticles comprise cesium doped indium oxide, tin doped indium oxide, or a combination thereof.

The plasmonic or high-index dielectric nanoparticle can comprise a high-index dielectric material. The high-index dielectric material can comprise silicon (n=3.4), silicon carbide (n=2.6), diamond (n=2.5), strontium titanite (n=2.4), cubic zirconia (n=2.2), zinc oxide (n=2.4), gallium phosphide (n=3.5), gallium arsenide (n=3.9), germanium (n=4), or a combination thereof. Without intending to be bound by theory, it is believed that relative to crystals formed from plasmonic nanoparticles, crystals having the same lattice parameters as the plasmonic nanoparticle crystals, but being formed from high-index dielectric material, saturate to $R_{max}$ much more slowly (more layers are needed) and the bandwidths are narrower.

Figure 1:
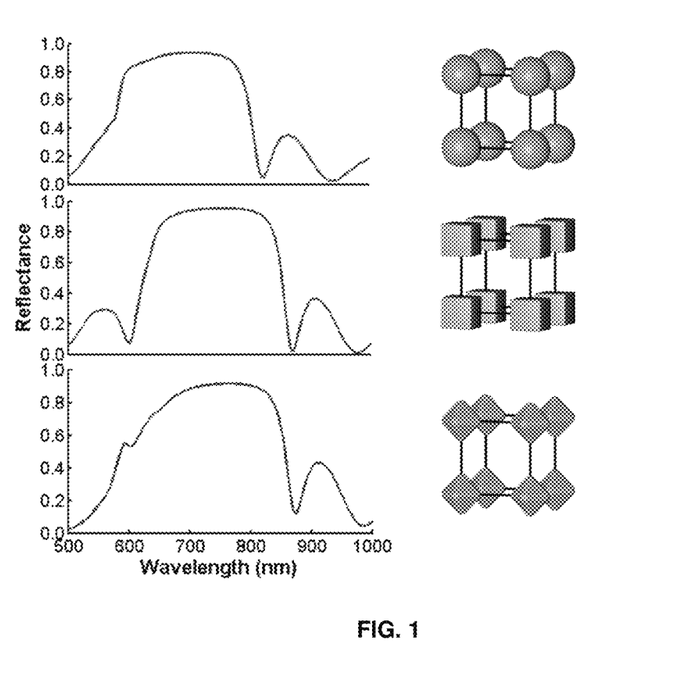
FIG. 1 shows the reflectance spectra of a simple cubic superlattice with spherical (top), cubic (middle), and octahedral (bottom) nanoparticles.

The shape of the nanoparticles that make up the photonic crystal is not particularly limited. Suitable nanoparticle shapes include, but are not limited to, spherical, cubic, octahedral, cylindrical, rhombic dodecahedral, prismatic, tetrahedral, rhombohedral, and combinations thereof. In embodiments, the shape of the nanoparticle is selected from the group consisting of spherical, cubic, octahedral, cylindrical, rhombic dodecahedral, prismatic, tetrahedral, rhombohedral, and a combination thereof. In embodiments, the shape of nanoparticle is selected from the group consisting of spherical, cubic, octahedral, and combinations thereof. As shown in FIG. 1, when comparing photonic crystals that are prepared from nanoparticles having the same volume and their corresponding superlattices having the same lattice constant, volume fraction, and number of nanoparticle layers, but different shape of the nanoparticle, the stopband exists in all reflectance spectra which indicates that the shape of the nanoparticle does not significantly affect the photonic properties of the photonic crystal. As used herein, superlattice refers to a lattice comprising multiple layers of nanoparticles regardless of the crystal symmetry or the presence or absence of photonic properties.

A periodic structure can be achieved by building a crystal where the nanoparticles are located at each lattice site. One, two, or each crystalline plane (e.g., the x-y plane, the y-z plane, or the x-z plane) can contain a layer of nanoparticles that serves as the high-index layer. The crystal can have different lattice symmetries and lattice constants, which in turn will affect the effective refractive index of the nanoparticle layer and the periodicity. The crystal lattice orientation of the nanoparticles in the photonic crystals is not particularly limiting. The nanoparticles can be arranged in a crystal symmetry along an axis parallel to the incident light (i.e., light propagation direction), selected from the group consisting of cubic, body-centered cubic, face-centered cubic, trigonal, tetragonal, body-centered tetragonal, orthorhombic, body-centered orthorhombic, face-centered orthorhombic, base-centered orthorhombic, hexagonal, monoclinic, base-centered monoclinic, and a combination thereof.

Figure 2A:
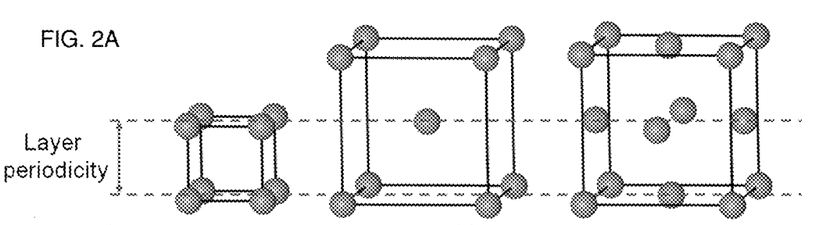
FIG. 2A shows layer periodicity corresponds to the spacing between two adjacent layers that contain nanoparticles rather than the lattice constant, wherein the lattice constant within each layer is kept constant at 200 nm.
Figure 2B:
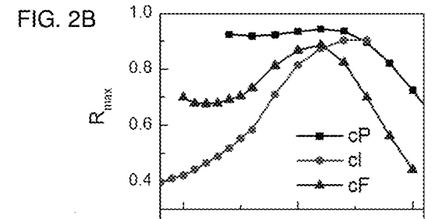
FIG. 2B shows the dependence of $R_{max}$ on the layer periodicity of simple cubic (cP), body-centered-cubic (cI), and face-centered-cubic superlattices (cF), wherein the lattice constant within each layer is kept constant at 200 nm.
Figure 2C:
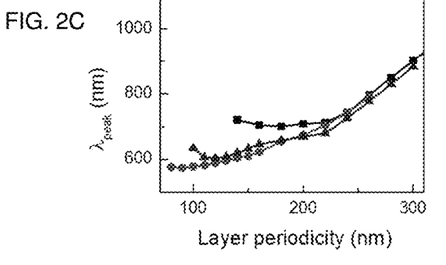
FIG. 2C shows the dependence on the center wavelength on the layer periodicity of cP, cI, and cF superlattices, wherein the lattice constant within each layer is kept constant at 200 nm.

Without intending to be bound by theory, it is believed that the maximum reflectance, $R_{max}$, of the stopband and the center wavelength, $\lambda_0$, are functions of the periodicity of each layer of nanoparticle along the light propagation direction, rather than the lattice constant of the crystal lattice of the nanoparticles in the light propagation direction. For example, a single body-centered-cubic (cI) or face-centered-cubic (cF) unit cell has three layers (top, middle, bottom), and the periodicity of each layer in the light propagation direction is half of the lattice constant (FIG. 2A). A clear trend between the center wavelengths and layer periodicity is observed between the three lattice types (FIGS. 2B and 2C). Surprisingly, the center wavelengths and maximum reflectance of each lattice type share similar values and trends, especially above 200 nm layer periodicity. As the layer periodicity increases, the center wavelengths increase, and $R_{max}$ increases until reaching a maximum value, then decreases. This demonstrates the importance of controlling the lattice constant (thus controlling the layer periodicity), which is not easily achievable with conventional fabrication techniques. The lattice constant and/or the periodicity of the photonic crystals described herein can be controlled by selecting a spacer group having a length such that the resulting lattice constant and/or periodicity corresponds to the desired lattice constant and/or desired periodicity. When center wavelengths and maximum reflectance are plotted as a function of lattice constant the correspondence between the three lattice types becomes weak, suggesting that instead of the lattice constant in the light propagation directions, the spacing between each nanoparticle layer in the light propagation direction (layer periodicity) should be considered as the periodicity of the photonic crystal. Although the "light propagation direction" is descriptive of the orientation of the photonic crystal in one dimension, it is understood that the "light propagation direction" can be any and/or all of the dimensions of the three-dimensional photonic crystal.

Figure 2D:
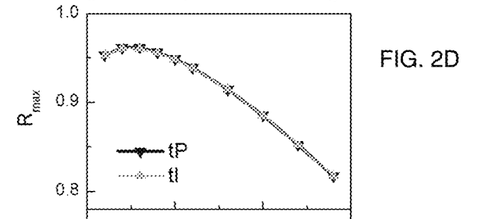
FIG. 2D shows the dependence of $R_{max}$ on the layer periodicity of tetragonal (tP) and body-centered-tetragonal (tI) superlattices, wherein the lattice constant within each layer is kept constant at 200 nm.
Figure 2E:
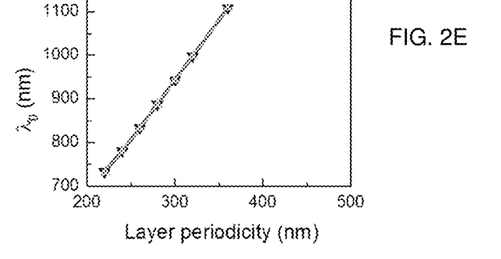
FIG. 2E shows the dependence on the center wavelength on the layer periodicity of tP and tI superlattices, wherein the lattice constant within each layer is kept constant at 200 nm.

Investigation of the center wavelength and $R_{max}$ for the tetragonal (tP) and body-centered-tetragonal (tI) unit cells confirmed that the center wavelength and $R_{max}$ are dependent on the layer periodicity rather than the lattice constant (FIG. 2D). FIG. 2E shows that the center wavelength depends linearly on the layer periodicity. Surprisingly, the properties of the body-centered-tetragonal (tI) lattices are almost identical to a tetragonal (tP) counterpart with the same layer periodicity (which for body-centered or face-centered lattices is half the lattice constant).

In general, when the layer periodicity in the light propagation direction is kept constant, as the lattice constant in the direction normal to incident light increases, $R_{max}$ and $\lambda_0$ decrease, due to the reduced index contrast between the nanoparticle and the spacer group and/or dielectric medium, as the amount of plasmonic or high index dielectric material is diluted in the nanoparticle layer. Although the "direction normal to incident light" and the "layer(s) normal to incident light" are descriptive of the orientation of the photonic crystal in one dimension, it is understood that "normal to the incident light" can be with respect to any and/or all of the dimensions of the three-dimensional photonic crystal. Because different lattice types have different nanoparticle arrangements in each layer, for example, squares, rectangles, and diamonds for tetragonal (tP), orthorhombic (oP), and hexagonal (hP), respectively, the volume fraction of a layer provided by the nanoparticles was used to determine the dependency of center wavelength and $R_{max}$ on the amount of nanoparticle present in a given layer, to allow for comparison between different lattice symmetries. As used herein and unless specified otherwise, the volume fraction of the nanoparticles in a given layer refers to the total volume of space taken up in the layer by the nanoparticles divided by the total volume of the layer. The volume fraction of the nanoparticles in a given layer can be determined, e.g., for a spherical nanoparticle, according to the equation:

$$(NP * V_{sphere})/(A*(2r))$$

wherein NP is the number of nanoparticles in each unit cell, $V_{sphere}$ is the volume of the nanoparticle, and A*(2r) is the volume of a unit cell, where A is the area of the facet in the x-y plane (normal to the incident light) of the unit cell, r is the radius of the nanoparticle, and thus the diameter of the nanoparticle defines the thickness of the nanoparticle layer.

Figure 3A:
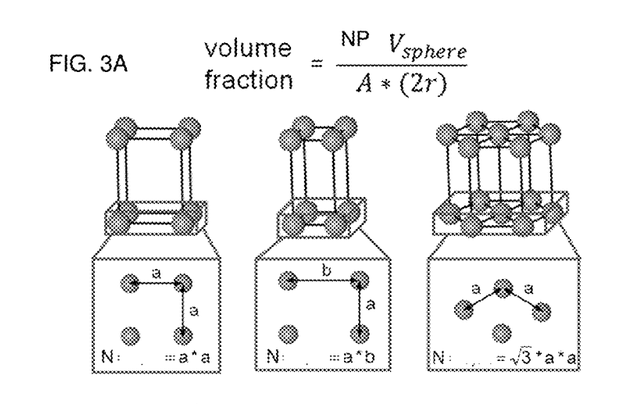
FIG. 3A shows the dependence of $R_{max}$, $\lambda_0$, and $\Delta\lambda_0/\lambda_0$ on the volume fraction, wherein the volume fraction is defined in the top equation where NP is the number of nanoparticles in each unit cell, $V_{sphere}$ is the volume of the nanoparticle, and A*(2r) is the volume of a unit cell in the nanoparticle layer, where A is the area of the facet in the x-y plane of the unit cell and r is the radius of the nanoparticle.
Figure 3B:
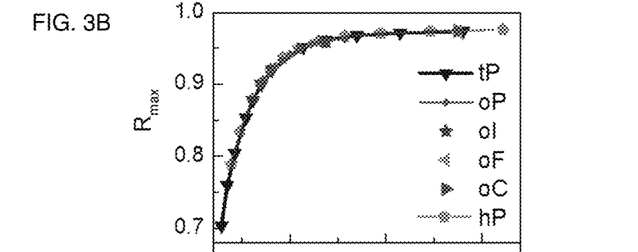
FIG. 3B shows the relationship between $R_{max}$ and volume fraction within each nanoparticle layer in tetragonal (tP), orthorhombic (oP), and hexagonal (hP) lattices.
Figure 3C:
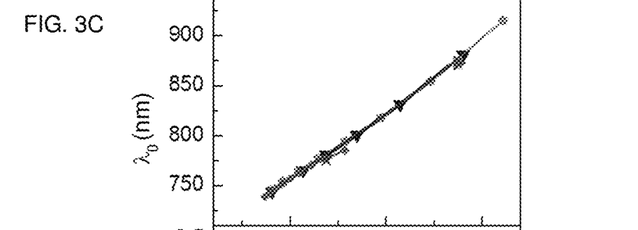
FIG. 3C shows the relationship between $\lambda_0$ and volume fraction within each nanoparticle layer in tetragonal (tP), orthorhombic (oP), and hexagonal (hP) lattices.
Figure 3D:
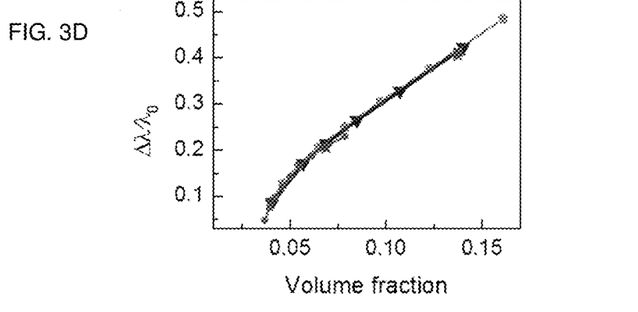
FIG. 3D shows the relationship between $\Delta\lambda_0/\lambda_0$ and volume fraction within each nanoparticle layer in tetragonal (tP), orthorhombic (oP), and hexagonal (hP) lattices.
Figure 4A:
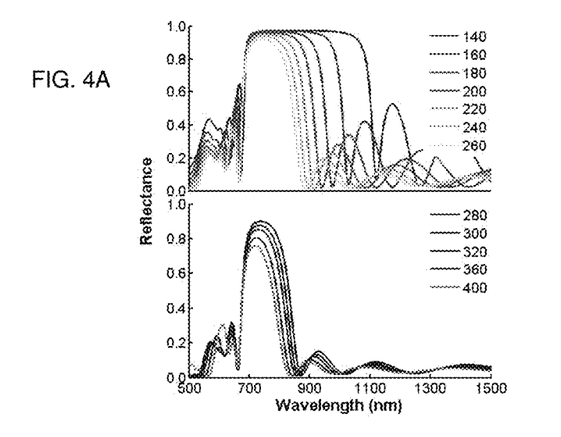
FIG. 4A shows the dependence of the reflectance spectra on the volume fraction of nanoparticles in each layer of tP lattices.
Figure 4B:
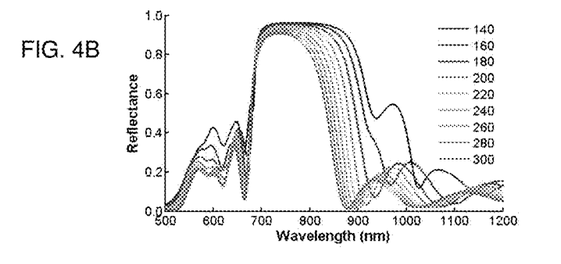
FIG. 4B shows the dependence of the reflectance spectra on the volume fraction of nanoparticles in each layer of oP lattices.
Figure 4C:
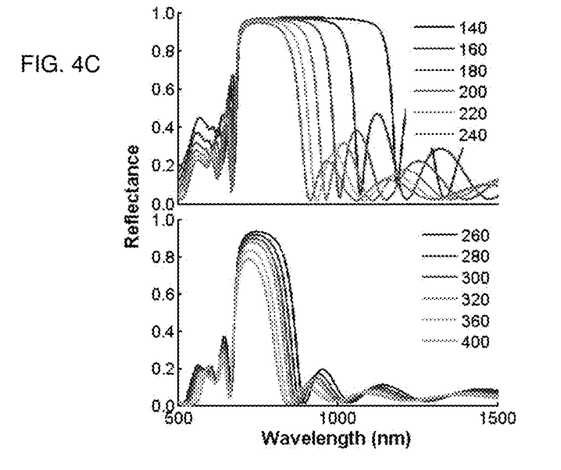
FIG. 4C shows the dependence of the reflectance spectra on the volume fraction of nanoparticles in each layer of hP lattices.

As shown in FIG. 3A, it was surprisingly found that the plots for $R_{max}$, $\lambda_0$, and normalized bandwidth ($\Delta\lambda/\lambda_0$) as a function of the volume fraction within each nanoparticle layer overlapped for tetragonal (tP), orthorhombic (oP), and hexagonal (hP) lattices. Without intending to be bound by theory, it is believed that the overlap in center wavelength, $R_{max}$, and normalized bandwidth for all three different lattice structures suggests that the stopband is dictated by the volume fraction rather than the exact arrangement of the nanoparticles within each layer for fixed nanoparticle size and layer periodicity. As shown in FIG. 3B, as the volume fraction increases, the $R_{max}$ increases monotonically until saturation. Moreover, $\lambda_0$ and the width of the band gap increased with increasing volume fraction (decreasing lattice constant in the direction normal to the incident light) and as shown in FIG. 4, this is a consequence of the low-energy band edge experiencing a blue-shift while the high-energy band edge remained relatively unchanged.

In general, the volume fraction of nanoparticles in a layer of the photonic crystal that is normal to an incident light can be any volume fraction which provides an $R_{max}$ value of greater than or equal to 0.80 when the photonic crystal is irradiated with the incident light having a wavelength $\lambda_0$. In embodiments, the volume fraction of the nanoparticles in a layer of the photonic crystal that is normal to an incident light having a wavelength of $\lambda_0$ is greater than 0 and less than or equal to 0.78, greater than 0 and less than or equal to 0.70, greater than 0 and less than or equal to 0.60, greater than 0 and less than or equal to 0.50, greater than 0 and less than or equal to 0.45, greater than 0 and less than or equal to 0.40, greater than 0 and less than or equal to 0.35, greater than 0 and less than or equal to 0.30, greater than 0 and less than or equal to 0.25, greater than 0 and less than or equal to 0.20, for example 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.22, 0.24, 0.26, 0.28, 0.30, 0.35, 0.40, 0.45, 0.50, 0.55, 0.60, 0.65, 0.70, 0.75, or 0.78. When the volume fraction of the nanoparticles in a layer of the photonic crystal normal to the incident light is greater than 0 and less than 0.78, for example in a range of greater than 0 and less than or equal to 0.20, the photonic crystal advantageously provides a balance between providing good dielectric contrast between the nanoparticles and the spacer group and/or dielectric medium while providing a large bandwidth for the stopband gap. The volume fraction of the nanoparticles in a layer of photonic crystal can be modified based on the length of the spacer group and/or the volume of the nanoparticle. For a given nanoparticle volume, the spacer group length needed to provide a desired volume fraction can be calculated.

Since the volume fraction, rather than the exact arrangement of the nanoparticles, within each nanoparticle layer affects the properties of the stopband, one can use the Maxwell-Garnett Effective Medium Theory (EMT) to obtain the effective index $n_{eff}$ of the nanoparticle layer, followed by using the Transfer Matrix Method (TMM), as commonly used in layered dielectric films, to calculate the reflectance and transmittance of the superlattices. The $n_{eff}$ is only dependent on the dielectric constants of the composite materials and the volume fraction by the equation:

$$\frac{\varepsilon_{eff} - \varepsilon_{matrix}}{\varepsilon_{eff} + 2\varepsilon_{matrix}} = FF * \frac{\varepsilon_{NP} - \varepsilon_{matrix}}{\varepsilon_{NP} + 2\varepsilon_{matrix}} \quad (4)$$

where FF is the fill factor (volume fraction of nanoparticle) in each layer. $\varepsilon_{NP}$ and $\varepsilon_{matrix}$ are the dielectric constant of the nanoparticle and the background matrix. The $\varepsilon_{eff}$ is the effective dielectric constant of the layer and $n_{eff}$ can then be calculated as the square root of $\varepsilon_{eff}$. The larger the volume fraction, the larger the real part of $n_{eff}$, which is important since large index contrast is desired. Once both $n_{eff}$ and $n_{matrix}$ are known, the reflectance, transmittance, and absorbance of the layered structure can be calculated using TMM. Accordingly, the method of the disclosure advantageously not only provides local control over detailed nanoscale properties at the nanoscale, but the macroscopic properties of the NP ensemble, such as its effective refractive index ($n_{eff}$), can also be tuned by various structural parameters. Also, the optical response associated with plasmonic nanoparticles is so strong that it is possible to use lattices with relatively low volume fraction in constructing functional photonic lattices. Although a high effective index can be realized in known plasmonic nanoparticle ensembles, large stopbands are not typically observed in such structures due to the dense-packed arrangements of NPs. Thus, the methods disclosed herein can advantageously be designed to provide photonic crystals comprising a high effective index in combination with a large stopband.

Advantageously, the nanoparticles present in the photonic crystal are not touching or interconnected. Separation of the nanoparticles provides one or more advantages, for example, maximizing the amount of distinct high- and low-index layers and/or maximizing the index contrast between the high- and low-index materials.

Figure 5:
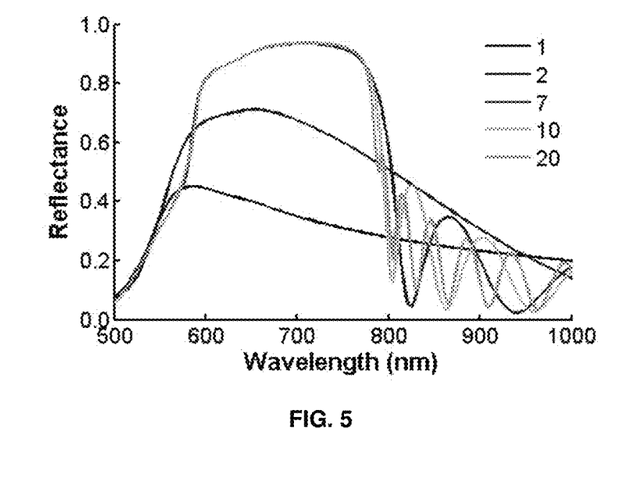
FIG. 5 shows the thickness dependence of the reflectance spectra for a cubic lattice of spherical nanoparticles having a radius of 54 nm and a lattice constant of 200 nm. When there is only one layer, the structure is not periodic and no Bragg reflection occurs. As the number of layers increases, the stopband appears and saturates at 7 layers for this superlattice.
Figure 6:
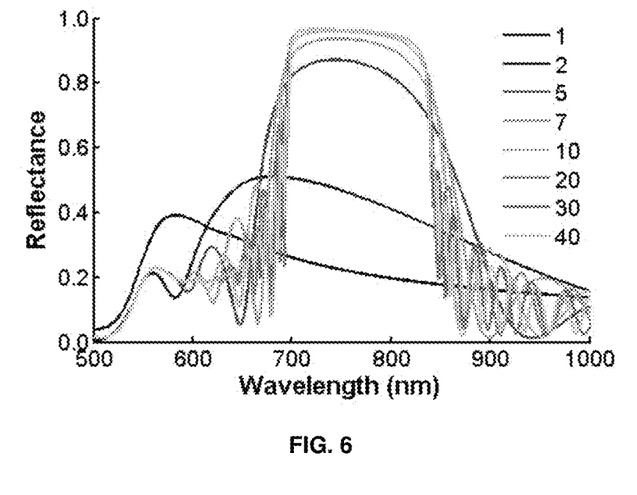
FIG. 6 shows the thickness dependence of the reflectance spectra for a cubic lattice of spherical nanoparticles having a radius of 54 nm and a lattice constant of 240 nm. As the number of layers increases, the stopband appears and does not saturate until the number of layers exceeds 10.

Without intending to be bound by theory, it is believed that the maximum reflectance, $R_{max}$, of the stopband is further a function of the number of nanoparticle layers (N) in the photonic crystal, that will be normal to the incident light upon irradiation. The number of nanoparticle layers is generally selected such that $R_{max}$ is greater than or equal to 0.8 when the photonic crystal is irradiated with incident light have a wavelength $\lambda_0$. As shown in FIG. 5, when there is only one layer of nanoparticles, the structure is not periodic in the light propagation direction and, therefore, no Bragg reflection occurs. As the number of layers increases, the stopband appears and saturates quickly. The number of layers at which the stopband saturates to a level of 0.80 or greater is generally the minimum number of nanoparticle layers which provide a structure having photonic properties. As the lattice constant increases, the number of layers provided to reach saturation of the reflectance band increases (FIG. 6). The number of nanoparticle layers normal to the incident light that provide a structure having photonic properties can be in a range of 3 to 50 layers, for example, 3 to 50 layers, 3 to 45 layers, 3 to 40 layers, 3 to 35 layers, 3 to 30 layers, 3 to 25 layers, 3 to 20 layers, or 3 to 15 layers.

The radius of the nanoparticles can also be modified in order to modify the center wavelength and bandwidth of the stopband. In general, the larger the nanoparticle size, the more the stopband is shifted to the red, regardless of volume fraction. Without intending to be bound by theory it is believed that the redshift is observed because at a constant volume faction, the layer periodicity is larger for larger nanoparticle size, causing the center wavelength to increase as predicted by equation (4). Further, in general, as the volume fraction increases for a given particle size, the center wavelength blue shifts and the stopband broadens. Larger nanoparticles (e.g., 50 nm or more) demonstrate a greater increase in stopband width relative to smaller nanoparticles (e.g., 49 nm or less), at a given volume fraction. Without intending to be bound by theory it is believed that at a sufficient volume fraction, both the $R_{max}$ and the width of the stopband increases with increased nanoparticle size. Thus, the nanoparticle size can be selected based on the desired optical properties of the photonic crystal. The size of the nanoparticle can be in a range of about 1 nm to about 1000 nm, for example, about 10 nm to about 900 nm, about 10 nm to about 800 nm, about 10 nm to about 700 nm, about 10 nm to about 600 nm, about 10 nm to about 500 nm, about 20 nm to about 400 nm, about 30 nm to about 300 nm, about 40 nm to about 200 nm, about 50 to about 100 nm, about 10 nm to about 90 nm, about 10 nm to about 50 nm, about 50 nm to about 90 nm, about 20 nm to about 80 nm, about 30 nm to about 70 nm, about 40 nm to about 60 nm, about 50 nm to about 58 nm, or about 52 nm to about 56 nm.

The nanoparticle registry between layers of nanoparticles was considered to determine if the exact arrangement of nanoparticles in each layer affects the stopband features of the photonic crystal. Registry was found to not affect the stopband features of the lattice which suggests that the relative arrangement of nanoparticles in each layer and between layers of the photonic crystal is not limited.

Spacer Groups

The spacer group can be any spacer group having a refractive index, $n_l$, lower than the refractive index of the nanoparticle comprising a plasmonic or high-index dielectric nanoparticle, $n_h$. The refractive index of the spacer group, $n_l$, can be in a range of about 1 to 3, for example, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.

The function of the spacer group is, generally, to provide a material having a desired length, that can couple to two or more nanoparticles to provide a physical spatial barrier between nanoparticles to prevent contact between nanoparticles and control of the lattice parameters of the resulting photonic crystal. Suitable spacer groups include, but are not limited to, DNA, proteins, lipid vesicles, silica, polystyrene, polydimethylsiloxane, poly(methyl methacrylate, block copolymers, hydrogels, and combinations thereof.

As used herein, "couple" and "coupling" encompass any of covalent bond formation, hydrogen bond formation, ionic bond formation (e.g. electrostatic attraction), and van der Waals interactions, for example, through which a spacer group can adsorb to/adhere to/couple to/associate with a nanoparticle.

The spacer group has a length, d, which is selected such that the maximum reflectance in the reflectance spectrum of the resulting photonic crystal, $R_{max}$, is greater than or equal to 0.80 when the photonic crystal is irradiated with an incident light have a wavelength $\lambda_0$. The spacer group length, d, in any dimension can be in a range of about 10 nm to about 1000 nm, about 10 nm to about 900 nm, about 10 nm to about 800 nm, about 10 nm to about 700 nm, about 10 nm to about 600 nm, about 10 nm to about 500 nm, about 10 nm to about 400 nm, about 10 nm to about 300 nm, about 10 nm to about 100 nm, about 10 nm to about 150 nm, for example, about 20 nm to about 150 nm, about 30 nm to about 150 nm, about 40 nm to about 150 nm, about 50 nm to about 150 nm, about 60 nm to about 150 nm, about 70 nm to about 150 nm, about 80 nm to about 150 nm, about 90 nm to about 150 nm, about 100 nm to about 150 nm, about 110 nm to about 150 nm, about 120 nm to about 150 nm, about 10 nm to about 145 nm, about 20 nm to about 140 nm, about 30 nm to about 135 nm, about 40 nm to about 140 nm, about 50 nm to about 140 nm, about 100 nm to about 140 nm, about 110 nm to about 145 nm, about 120 nm to about 140 nm, or about 130 nm to about 135 nm.

The length of the spacer group can be the same or different in each dimension of the photonic crystal. For example, in embodiments wherein the length of the spacer group is the same in each dimension, the photonic crystal will have a cubic lattice. In some embodiments, the length of the spacer group in at least one dimension will be different from the length of the spacer groups in the other two dimensions. In some embodiments, the length of the spacer groups will be different between all three dimensions.

As previously described, the maximum reflectance, $R_{max}$, of the stopband and the center wavelength at which $R_{max}$ is observed are functions of the periodicity of the photonic crystal in the direction of light propagation; $R_{max}$ is further a function of the number of layers of nanoparticles, N, in the light propagation direction of the photonic crystal; and $R_{max}$, the center wavelength of the stopband, and the bandwidth of the stopband are functions of the volume fraction of the nanoparticles in the nanoparticle layers of the photonic crystal that are normal to the incident light. Accordingly, the optical properties of the photonic crystal can be controlled by selecting and/or modifying the parameters of the crystal lattice, in particular, the periodicity of the photonic crystal in the direction of light propagation, the number of layers of nanoparticles in the light propagation direction, and/or the volume fraction of the nanoparticles in the nanoparticle layers of the photonic crystal that are normal to the incident light. The periodicity of the photonic crystal in the light propagation direction and the volume fraction of nanoparticles in the layers normal to the incident light can be tuned by modifying the length of the spacer group. For example, the periodicity in the light propagation direction can be increased by increasing the length of the spacer group, d, and decreased by providing a shorter spacer group. Similarly, the volume fraction of nanoparticles can be increased by shortening the length of the spacer group, d, and decreased by lengthening the spacer group.

In view of the relationship between periodicity in the light propagation direction, nanoparticle volume fraction in the layers normal to the incident light, and the number of layers in the light propagation direction, three-dimensional photonic crystals can be constructed to demonstrate properties of interest for a given application. For example, if a thin photonic crystal is of interest, the number of nanoparticle layers can be minimized and the periodicity and/or nanoparticle volume fraction selected to provide an $R_{max}$ value of at least 0.8 or greater. As another example, if a photonic crystal having a photonic band gap at a specific wavelength, e.g., $\lambda_0$, is of interest, the periodicity of the photonic crystal in the light propagation direction can be selected to provide $\lambda_0$ as the center wavelength at which $R_{max}$ is observed, and the number of nanoparticle layers in the light propagation direction and/or the volume fraction of the nanoparticles in the layers normal to the incident light can be selected to provide an $R_{max}$ value of at least 0.8 or greater. As a further example, if a photonic crystal have a broad (or narrow) bandwidth for the photonic band gap is of interest, the volume fraction of the nanoparticles in the layers normal to the incident light can be selected to provide the desired bandwidth, and the periodicity and/or number of layers of nanoparticles can be selected to provide an $R_{max}$ value of at least 0.8 or greater.

The optical properties of the photonic crystals can be the same or different in the different dimensions. For example, the optical properties can be the same in all three dimensions of the photonic crystal by providing a cubic lattice having the same number of nanoparticle layers, N, in each of the three dimensions. Alternatively, the optical properties can be different in at least one dimension of the photonic crystal by altering the length of the spacer group in at least one direction and/or modifying the number of nanoparticle layers, N, in at least one direction.

DNA Programmable Assembly

DNA-programmable assembly is one suitable method for making photonic crystals using DNA as the spacer group since it provides fine control and even sub-nm tunability over particle spacing. Moreover, interparticle spacing can be dynamically tuned after photonic crystal formation, enabling dynamic tuning of the stopband location.

Spacer groups comprising DNA have three components, an anchor strand, a linker strand, and a duplexer strand. The anchor strand comprises a DNA sequence including a functional group, such as a thiol, at one terminus which allows the anchor strand to be adsorbed onto or covalently or non-covalently bound to the nanoparticles. Suitable functional groups also include, but are not limited to, phosphate groups and amine groups. The anchor strand further include a region adjacent to the functional group which provides flexibility (e.g., a $A_{10}$ sequence (SEQ ID NO: 4)) and a hybridization region that comprises a sequence complementary to a region on the linker strand so as to allow hybridization between the two strands. The length of the flexible region can be varied to modify the DNA loading and tuning the flexibility of the DNA spacer group and the length of the hybridization region can be varied to correspond to the complementary region on the linker strand. For example, the flexible region can comprise 5-20 or 5-15 nucleotide bases, and the hybridization region can comprise 10-30, 10-25, 15-25, or 15-20 nucleotide bases.

The linker strand comprises three regions including (i) a sequence complementary to the hybridization region of the anchor strand, (ii) a spacer sequence which is designed for controlling the length of the DNA spacer group, and (iii) a self-complementary "sticky" end which controls the interaction between the assembling nanoparticles. Region (i) of the linker strand comprises the same number of nucleotide bases as the hybridization region of the anchor strand. Region (ii) can be selected to have a number of nucleotide bases in view of desired overall length of the spacer group. For example, the number of nucleotide bases in region (ii) of the linker strand can comprise 0 to 300 bases. Region (iii) can comprise 3-10, 3-6, or 4 nucleotide bases as long as the sequence of region (iii) is self-complementary.

The duplexer strand comprises a sequence that is complementary to the sequence of region (ii) of the linker strand, such that it can hybridize to the linker strand.

The complementarity of the sequences discussed above can be 100% complementary, or at least (meaning greater than or equal to) 95% complementary, at least 90%, at least 85%, at least 80%, at least 75%, at least 70%, at least 65%, at least 60%, at least 55%, or at least 50%.

Dielectric Medium

In some embodiments, the photonic crystal can be provided in a dielectric medium. The refractive index of the dielectric medium, nm, can be in a range of about 1 to 3, for example, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3. In embodiments, the refractive index of the dielectric medium is substantially the same as the refractive index of the spacer group, $n_f$. As used herein, and unless specified otherwise, the refractive indices of two materials are "substantially the same" when the difference between the refractive indices is 0.3 refractive index units or less, or 0.2 refractive index units or less, or 0.1 refractive index units or less. When the lattice parameters are fixed, the spectral location of the stopband can be tuned by immersing or embedding the crystal in different dielectric medium and the larger the refractive index of the dielectric medium, the broader the stopband. Thus, the bandwidth and center wavelength of the band gap of the photonic crystal can advantageously be tuned by choice of dielectric medium.

Exemplary dielectric media include, but are not limited to, silica, oil, water, organic solvent, liquid polymers, or a combination thereof. In embodiments, the dielectric medium comprises silica.

Methods of Preparing Photonic Crystals

Three-dimensional photonic crystals having a band gap having a center wavelength, $\lambda_0$, in a range of about 300 nm to about 10 µm can be prepared. In embodiments, the center wavelength, $\lambda_0$, of the band gap is in a range of about 400 nm to about 700 nm. In embodiments, the center wavelength, $\lambda_0$, of the band gap is in a range of about 700 nm to about 10 µm.

The method of preparing three-dimensional photonic crystals according to the disclosure comprises (a) selecting a nanoparticle, wherein the nanoparticle comprises plasmonic or high-index dielectric nanoparticles having a refractive index, $n_h$, in a range of about 2 to about 30; (b) selecting a spacer group having a refractive index, $n_l$, in a range of about 1 to about 3, and a length, d, wherein $n_h$ is greater than $n_l$; and (c) admixing a plurality of the plasmonic or high-index nanoparticles and a plurality of spacer groups to form the three-dimensional photonic crystal comprising alternating plasmonic or high index nanoparticles and spacer groups; wherein (i) the spacer group length, d, is selected such that the maximum reflectance in the reflectance spectrum, $R_{max}$, is greater than or equal to 0.80 when the photonic crystal is irradiated with an incident light having a wavelength $\lambda_0$; and (ii) the photonic crystal comprises a number of plasmonic nanoparticle layers, N, normal to the incident light, such that $R_{max}$ is greater than or equal to 0.8 when the photonic crystal is irradiated with the incident light having a wavelength $\lambda_0$.

The nanoparticle and the spacer group having a refractive index, $n_l$, can be specifically selected to provide a crystal having a band gap having a center wavelength, $\lambda_0$, in a range of 300 nm to 10 µm. For example, in the case of a cubic lattice structure (providing the same photonic properties in all three dimensions), the length of the spacer group needed to provide a photonic crystal having a band gap with a center wavelength ($\lambda_0$) of about 750 nm, for example, can be estimated according to Equation (1), $\lambda_0/4$, or about 187.5 nm. In this example, the length of the spacer group (and resulting layer periodicity) corresponds to the lattice constant. In view of the determined lattice constant, for a selected nanoparticle having a given radius (r), the volume fraction of the nanoparticles in a given layer can be calculated according to the equation $$(NP * V_{sphere})/(A*(2r))$$

wherein NP is the number of nanoparticles in each unit cell, $V_{sphere}$ is the volume of the nanoparticle, and $A*(2r)$ is the volume of a unit cell, where A is the area of the facet in the x-y plane of the unit cell and r is the radius of the nanoparticle. Thus, for a silver nanoparticle having a 50 nm radius, the calculated volume fraction is about 0.15. Equation (4) can then be used to estimate the effective refractive index across a range of wavelengths, and a theoretical calculation (such as TMM) or a simulation (such as FDTD) can be used to plot the reflectance spectrum and observe the location of the stopband. If the center wavelength is longer or shorter than 750 nm, the trial lattice constant can be modified until the center wavelength is at 750 nm. The number of layers can then be adjusted, if necessary, to provide a lattice having a band gap with a center wavelength of 750 nm and an $R_{max}$ of at least 0.80.

Methods of forming nanoparticle superlattices by admixing nanoparticles with spacer groups are known in the art. The nanoparticles and spacer groups are admixed under conditions sufficient to couple the spacer group to at least two nanoparticles. Admixing can comprise incubating mixtures of nanoparticles and spacer groups at room temperature and/or heating mixtures of nanoparticles and spacer groups (or aggregates thereof) followed by slowly cooling to room temperature to prepare superlattices.

Optionally, admixing can include admixing the nanoparticles and the spacer groups in the presence of a dielectric medium. Generally, the index of refraction of the dielectric medium is substantially the same as the index of refraction of the spacer group.

In embodiments, admixing comprises admixing the plurality of nanoparticles and plurality of DNA anchor strands to form a plurality of functionalized nanoparticles; admixing a plurality of DNA linker strands with a plurality of DNA duplexer strands in solution to form a duplexed DNA linker solution; and admixing the duplexed DNA linker solution with the plurality of functionalized nanoparticles to form the three-dimensional photonic crystal. The admixing of the plurality of nanoparticles and plurality of DNA anchor strands to form a plurality of functionalized nanoparticles can be performed prior to, after, or concurrently with the admixing of a plurality of DNA linker strands with a plurality of DNA duplexer strands in solution to form a duplexed DNA linker solution.

In embodiments, the method further comprises depositing the three-dimensional photonic crystal on a substrate. The substrate is not particularly limiting and the appropriate substrate can be selected based on the desired end-use of the photonic crystal, e.g., semiconductor lasers, optical integrated circuits, optical switches, solar cells, light emitting diodes, sensors, and optical fibers. Suitable substrates include, but are not limited to, glass, glass coated with indium tin oxide, silicon, silicon nitride, aluminum oxide, and combinations thereof.

The three-dimensional photonic crystal can be deposited on the substrate using any technique known in the art. For example, the three-dimensional photonic crystal can be embedded in silica and drop cast onto the substrate. Alternatively, the photonic crystal can be grown on the substrate with defined size and location by patterning the substrate.

In some embodiments, the method provides a three-dimensional photonic crystal having a band gap having a center wavelength, $\lambda_0$, in a range of about 300 nm to about 10 µm, including admixing a plurality of plasmonic gold nanoparticles and a plurality of spacer groups comprising DNA, wherein the length of the spacer group, d, is about 134 nm to provide a photonic crystal, wherein the photonic crystal comprises 20 nanoparticle layers, N, and the maximum reflectivity is greater than or equal to 0.80 when the photonic crystal is irradiated with an incident light having a wavelength $\lambda_0$.

Finite-Difference Time-Domain (FDTD) Simulation

FDTD simulations were run with a commercial package Lumerical FDTD Solutions v.8.12.631. The dielectric functions of gold, silver, aluminum and copper were adopted from the experimental data obtained by Johnson and Christy, "Optical constants of the noble metals." Phys. Rev. B 6, 4370-4379 (1972), Shiles et al., "Self-consistency and sum-rule tests in the Kramers-Kronig analysis of optical data: Applications to aluminum." Phys. Rev. B 22, 1612-1628 (1980) and Hagemann et al., "Optical constants from the far infrared to the x-ray region: Mg, Al, Cu, Ag, Au, Bi, C, and $Al_2O_3$." J. Opt. Soc. Am. 65, 742-744 (1975), respectively, each of which is herein incorporated by reference in its entirety. The refractive index of silica was assumed to be 1.46. In order to obtain the reflectance spectra, an infinite thin slab model was used, unless otherwise specified, where periodic boundary conditions were adopted in the x and y directions such that a simple cubic unit cell was repeated infinitely in the x-y plane. A perfectly matched layer boundary condition was used in the z direction, which was also the light propagation direction. The length of the superlattice in the z direction was determined by the number of layers and the lattice constant in the z direction. The infinite thin slab model assumes that only the center of the reflected light is collected, namely not counting light reflected at the edge and side of the photonic crystals. The validity of this model for the experimental setup and DNA-nanoparticle (NP) superlattice was previously demonstrated in the literature.[4] Illumination with light occurs in air ($n_0$=1), and the crystal is assumed to lie on top of a glass substrate ($n_s$=1.44). For band-structure calculations, a single unit cell for the simple cubic lattices and four unit cells for the diamond lattice were simulated with Bloch boundary conditions. More than ten dipole sources with random orientation and location within the simulation region were used to excite all optical modes in the lattices. More than ten randomly located time monitors were used to collect the signal in the time domain, and Fourier transform was performed to convert data into the frequency domain.

The photonic crystals and methods of making the photonic crystals in accordance with the disclosure can be better understood in light of the following examples, which are merely intended to illustrate the photonic crystals and are not meant to limit the scope thereof in any way.

EXAMPLES

Example 1

Nanoparticle Synthesis and Characterization

Gold nanocubes (88 nm edge length, >95% were cube shaped with a <5% variation in size) were synthesized according to a seed-mediated method as described in "Universal noble metal nanoparticle seeds realized through iterative reductive growth and oxidative dissolution reactions." J. Am. Chem. Soc. 136, 7603-7606 (2014), herein incorporated by reference in its entirety. The uniform seeds prepared via iterative reductive growth and oxidative dissolution reactions are critical to the uniformity of the final products. Particle uniformity was characterized based on statistical analysis of Hitachi H8100 transmission electron microscope (TEM) images.

DNA Design, Synthesis and Purification

Detailed DNA sequences can be found in Table 1. The DNA strands have three key components: an anchor strand, a linker strand, and duplexer strands. The anchor strand with a thiol group allowed them to be adsorbed onto gold nanoparticles, a $dA_{10}$ region that increased the flexibility and a region that hybridized to the linker strand. The linker strand contained three regions: an 18-base sequence complementary to the hybridization region of the anchor strand; some repeated 40-base spacer sequences which are designed for conveniently controlling the length of the "DNA bonds"; and a 4-base self-complementary sticky end which determines the interaction between the assembling nanoparticles. Each region is separated by a single base A to provide some flexibility. The duplexer strands can hybridize to the 40-base spacer sequences in the linker strand.

|  | DNA SEQUENCE (5'-3') | NUMBER OF BASE |
| --- | --- | --- |
| ANCHOR STRAND | TCA ACT ATT CCT ACC TAC AAA AAA AAA A SH (SEQ ID NO: 1) | 28 |
| LINKER STRAND | GTA GGT AGG AAT AGT TGA A TTTTTTTTTTTT ACT GAG CAG CAC TGA TTTTTTTTTTTT A GCGC (SEQ ID NO: 2) | 64 |
| DUPLEXER STRAND | AAAAAAAAAAAA TCA GTG CTG CTC AGT AAAAAAAAAAAA (SEQ ID NO: 3) | 40 |

DNA strands were synthesized on a solid-support with a MM48 synthesizer (BioAutomation) (or equivalent) on a solid-support with reagents purchased from Glen Research and purified via reverse-phase high-performance liquid chromatography (HPLC; Agilent). Matrix-assisted laser desorption ionization time-of-flight mass spectrometry (MALDI-TOF-MS) was used to confirm the molecular weight and purity of HPLC-purified DNA. Concentration was determined by UV-vis spectrometry. The extinction coefficient of each DNA strand was calculated with Oligo-Analyzer tool from Integrated DNA Technologies.

Nanoparticle Functionalization and Assembly

The gold nanocubes were chemically functionalized with anchor strands through well-known literature procedures. In short, the as-synthesized nanocubes were collected by centrifugation and washed with $H_2O$. This process was repeated. After removing the supernatant, the colloid was re-dispersed in an aqueous solution of the desalted anchor strand (2 $OD_{260}$ of DNA for 1 $OD_{SPR}$ of nanocube). Prior to use, this strand was maintained in the reduced state with dithiothreitol (DTT, Sigma Aldrich). Both the DTT and salt must be removed prior to particle modification. Then, the mixture was brought into 0.01 M phosphate buffer solution (PBS) and 0.01% sodium dodecyl sulfate (SDS) solution and was agitated on a shaker (~1000 rpm) for 0.5 hour. The nanocubes were then treated by slow addition of NaCl, which lead to increased DNA loading. The salt concentration of the nanocube solution was successively increased from 0.05 M to 0.1 M to 0.2 M to 0.3 M to 0.4 M to 0.5 M NaCl using a 2 M NaCl stock solution. These additions were done sequentially with 10 s sonication and 0.5 hour shaking between each salt addition. The colloid was treated with overnight shaking after the final salt addition to insure maximum DNA loading. Free DNA strands were removed by three rounds of centrifugation with 0.01% SDS solution. The final pellet was re-suspended in a solution containing 0.01% SDS, 0.01 M PBS and 0.5 M NaCl.

In a separate vessel, the DNA linker strand was mixed with duplexer strand in a solution containing 0.5 M NaCl and 0.01 M PBS, and then was incubated at 40° C. for 0.5 hour for pre-hybridization. The duplexed DNA linker solution was then added into the functionalized nanocube colloid in excess to the amount of the anchor strands on particle surface. The mixture was allowed to incubate overnight at room temperature to form aggregates. 150 μL solutions with aggregates were pipetted into 150 μL PCR 8-tube strips (Life Technologies) and placed into a thermal cycler (Life Technologies). The temperature of the thermal cycler was first increased to 60° C., and then slowly cooled to room temperature in a rate of 0.1° C. per 10 minutes. The slow cooling rate provides sufficient time for the superlattice to reach equilibrium during the assembly process.

Superlattice Characterization

Nanocube superlattices were embedded in silica before electron microscope, optical microscope and small angle X-ray scattering (SAXS) characterization. Briefly, 2 μL of N-trimethyoxysilylpropyl-N,N,N-trimethylammonium chloride (TMSPA) per ml of superlattice solution was added to as-synthesized superlattice solution and vigorously stirred for 20 minutes, followed by addition of 4 μL of tetraethyl orthosilicate (TEOS). The solution based superlattices were then stirred for more than 12 hours. Finally, the solution was purified by three rounds of centrifugation and re-suspension in water. This method can preserve crystal symmetry and lattice parameters when superlattices are transferred from solvent. Scanning electron microscope (SEM; Hitachi SU8030) and scanning transmission electron microscope (Hitach HD2300) were used to observe the morphologies of nanocube superlattice. SAXS experiments were used to determine lattice parameters. X-rays with $\lambda$=1.24 Å (E=10 keV) were used.

Optical Measurements

Silica embedded superlattices were first drop cast onto plasma cleaned Indium Tin Oxide (ITO) coated glass slides, and the solvent was fully evaporated, resulting in a population of superlattices with their flat surfaces lying parallel to the substrate. Superlattices were then observed and located with both a Zeiss Axio Observer.Z1 microscope (or equivalent) and a Hitachi SU8030 SEM (or equivalent) to ensure proper orientation and a flat top surface. A coverslip deposited with anti-reflection coating purchased from Evaporated Coatings Inc. was then fixed close to the sample by carbon tape at the corners. Subsequently, immersion oil with a refractive index matching that of silica was slowly injected in-between the coverslip and the glass slide, such that the samples were fully immersed in the oil. This effectively provides an optically homogeneous background for the silica-embedded superlattices. A Xenon lamp (XBO 75) with a broad-band spectrum (300-1100 nm) was used as the light source. In bright field (BF) reflection mode, the sizes of field-stop and aperture were minimized to minimize the angle of incident light. A 50× objective (N.A. 0.8) was used to collect light from only the center of the superlattices. A spectrometer with 50 g/mm grating (Princeton Instrument or equivalent) and a charge coupled device (PyLoN) were connected to the microscope and were used to collect the backscattering spectra. A slit (50 μm) was used to extract the backscattering spectrum from a thin line at the center of the superlattice, which enables the use of the thin slab model in FDTD to simulate this system. Finally, a background spectrum was chosen from a clean region near the superlattice and was used to remove the signal from the background in the backscattering spectrum.

Figure 8:
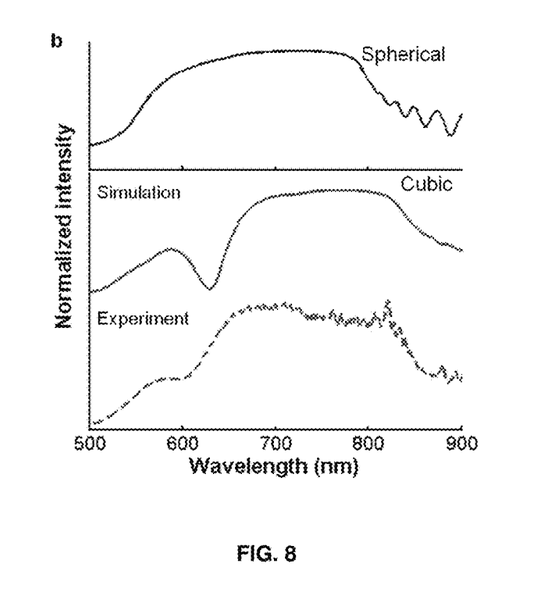
FIG. 8 shows the experimental measurement and FDTD simulations of cubic nanoparticle superlattices wherein (top) the nanoparticle is spherical and (bottom) the nanoparticle is cubic.

Thus, example 1 demonstrates the preparation and characterization of three-dimensional photonic crystal comprising micron-sized simple cubic superlattices with well-faceted cubic crystal habits made from DNA-functionalized cubic NPs. The lattice constant as measured by small angle X-ray scattering was 134 nm. The simulation results for a superlattice made of spherical NPs with the same volume and lattice constants show the existence of a broad stopband, a property that is observed both experimentally and through simulation in the cubic NP superlattice. Moreover, the experimentally observed stopband matches remarkably well with the simulation prediction, emphasizing that the design rules articulated above are not limited to spherical particles (FIG. 8).

Example 2

FDTD Simulations

Figure 7:
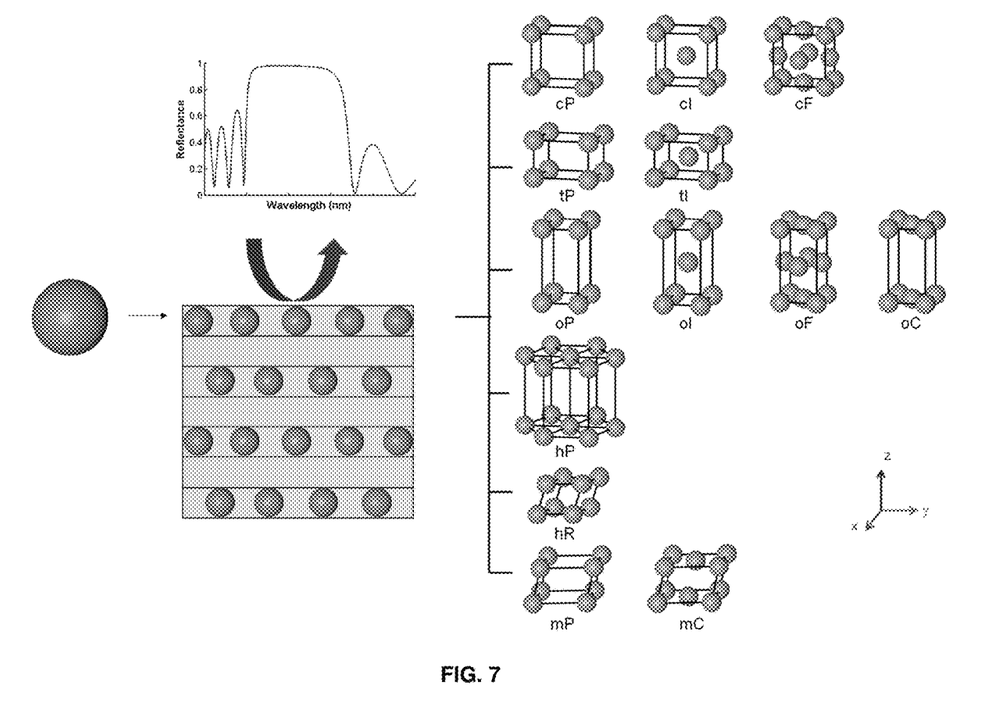
FIG. 7 is a schematic representation of one dimension of photonic crystals with gold nanoparticles. The stopband features are generated by light incident normal to the x-y plane. Along the z direction, the superlattice can be viewed as alternating nanoparticle and dielectric layers.

Finite-difference time-domain (FDTD) simulations were carried out to investigate how the lattice parameters of plasmonic photonic crystals—the lattice constants in all three dimensions and the angle—affect the photonic stopband features. Lattices were set up with spherical Au nanoparticles (diameter 108 nm), all embedded in a silica matrix (as such structures can be made experimentally). To minimize computational time and keep the simulations tractable, we found 7 layers of NPs sufficiently represented the thin plasmonic photonic crystal films and were used in all simulations unless otherwise specified. Normal incidence of light (z-direction, light propagation direction) onto the (001) plane (x-y plane, normal to the incident light) of the lattice was investigated (FIG. 7).

The foregoing description is given for clearness of understanding only, and no unnecessary limitations should be understood therefrom, as modifications within the scope of the invention may be apparent to those having ordinary skill in the art.

What is claimed:

1. A method of forming a three-dimensional photonic crystal having a band gap having a center wavelength, $\lambda_0$, in a range of about 300 nm to about 10 μm, comprising:
   (a) selecting a nanoparticle, wherein the nanoparticle comprises a plasmonic nanoparticle or a high index dielectric nanoparticle having a refractive index, $n_h$, in a range of about 2 to about 30;
   (b) selecting a spacer group having a refractive index, $n_l$, in a range of about 1 to about 3, and a length, d, wherein $n_h$ is greater than $n_l$; and
   (c) admixing a plurality of the nanoparticles and a plurality of spacer groups to form the three-dimensional photonic crystal comprising alternating nanoparticles and spacer groups;
   wherein
      (i) the spacer group length, d, is selected such that the maximum reflectance in the reflectance spectrum, $R_{max}$, is greater than or equal to 0.80 when the photonic crystal is irradiated with an incident light having a wavelength $\lambda_0$; and
      (ii) the photonic crystal comprises a number of nanoparticle layers, N, normal to the incident light, such that $R_{max}$ is greater than or equal to 0.8 when the photonic crystal is irradiated with the incident light having a wavelength $\lambda_0$.

2. The method of claim 1, wherein the difference between $n_h$ and $n_l$, $\Delta n$, is at least 0.1.

3. The method of claim 1, wherein the admixing further comprises admixing in the presence of a dielectric medium.

4. The method of claim 3, wherein the dielectric medium has an index of refraction, $n_m$, of 1 and 3.

5. The method of claim 3, wherein $n_m$ is substantially the same as $n_l$.

6. The method of claim 1, wherein the dielectric medium comprises silica, polymer, oil, water, organic solvent, or a combination thereof.

7. The method of claim 1, wherein the volume fraction of nanoparticles in a layer of the photonic crystal that is normal to the incident light having a wavelength $\lambda_0$ is greater than 0 and less than or equal to 0.2.

8. The method of claim 1, further comprising depositing the photonic crystal on a substrate.

9. The method of claim 8, wherein the substrate comprises glass, glass coated with indium tin oxide, silicon, silicon nitride, aluminum oxide or a combination thereof.

10. The method of claim 1, wherein the nanoparticles comprise a plasmonic metal selected from the group consisting of gold, silver, copper, platinum, palladium, nickel, aluminum, gallium, indium, lithium, sodium, potassium, rubidium, magnesium, calcium, strontium, doped metal oxides, and a combination thereof.

11. The method of claim 1, wherein the nanoparticles comprise gallium doped zinc oxide, aluminum doped zinc oxide, cesium doped indium oxide, tin doped indium oxide, or a combination thereof.

12. The method of claim 1, wherein the nanoparticles comprise a high-index dielectric material comprising silicon, silicon carbide, diamond, strontium titanite, cubic zirconia, zinc oxide, gallium phosphide, gallium arsenide, germanium, or a combination thereof.

13. The method of claim 1, wherein the spacer group comprises DNA, protein, lipid vesicles, block copolymers, silica, polystyrene, polydimethylsiloxane, poly(methyl methacrylate), or a combination thereof.

14. The method of claim 1, wherein the spacer group length, d, is about 10 nm to about 150 nm.

15. The method of claim 1, wherein the number of nanoparticle layers normal to the incident light, N, is 3 to 50.

16. The method of claim 1, wherein the nanoparticles in the photonic crystals are arranged in a crystal symmetry along an axis parallel to the incident light, and the crystal symmetry is selected from the group consisting of cubic, body-centered cubic, face-centered cubic, trigonal, tetragonal, body-centered tetragonal, orthorhombic, body-centered orthorhombic, face-centered orthorhombic, base-centered orthorhombic, hexagonal, monoclinic, base-centered monoclinic, and a combination thereof.

17. The method of claim 1, wherein the band gap has a center wavelength, $\lambda_0$, in a range of about 400 nm to about 700 nm.

18. The method of claim 1, wherein the band gap has a center wavelength, $\lambda_0$, in a range of about 700 nm to about 10 μm.

19. The method of claim 1, wherein the nanoparticles comprise plasmonic gold nanoparticles, the spacer group comprises DNA, the spacer group length, d, is about 134 nm, and N is 20.

20. The method of claim 1, wherein the admixing comprises:
   a. admixing the plurality of plasmonic nanoparticles and a plurality of DNA anchor strands to form a plurality of functionalized nanoparticles;
   b. admixing a plurality of DNA linker strands with a plurality of DNA duplexer strands in solution to form a duplexed DNA linker solution; and
   c. admixing the duplexed DNA linker solution with the plurality of functionalized nanoparticles to form the three-dimensional photonic crystal.

* * * * *